United States Patent [19]
Commandeur et al.

[11] Patent Number: 5,993,607
[45] Date of Patent: Nov. 30, 1999

[54] PROCESS FOR THE PURIFICATION OF CHLORINATED AROMATIC HYDROCARBONS

[75] Inventors: Raymond Commandeur, Vizille; Dominique Audoux, Sassenage, both of France

[73] Assignee: Elf Atochem, S.A., Puteaux, France

[21] Appl. No.: 09/058,166

[22] Filed: Apr. 10, 1998

[30] Foreign Application Priority Data

Apr. 10, 1997 [FR] France ................................. 97 04408

[51] Int. Cl.⁶ ....................................................... B01D 3/34
[52] U.S. Cl. ..................... 203/6; 203/7; 203/39; 203/73; 203/80; 203/DIG. 19; 203/99; 208/47; 208/262.1
[58] Field of Search .................. 203/39, 7, 4, 6, 203/80, 99, 73, DIG. 19; 208/262.1, 47; 585/950; 252/387; 422/7

[56] References Cited

FOREIGN PATENT DOCUMENTS

| | | |
|---|---|---|
| 0424847 | 5/1991 | European Pat. Off. . |
| 1230416 | 12/1966 | Germany . |
| 327557 | 11/1992 | Japan . |
| 9405610 | 3/1994 | WIPO . |

*Primary Examiner*—Virginia Manoharan
*Attorney, Agent, or Firm*—Millen, White, Zelano & Branigan, P.C.

[57] ABSTRACT

In a process for the purification by distillation of chlorinated aromatic hydrocarbons originating from the chlorination of aromatic hydrocarbons in the presence of $FeCl_3$, the crude reaction product is first partially degassed and then directly subjected to distillation in the presence of said $FeCl_3$.

16 Claims, No Drawings

PROCESS FOR THE PURIFICATION OF CHLORINATED AROMATIC HYDROCARBONS

FIELD OF THE INVENTION

The present invention relates to a process for the purification of chlorinated aromatic hydrocarbons, such as in particular trichlorobenzenes and dichlorotoluenes, obtained by chlorination of aromatic hydrocarbons in the presence of ferric chloride.

BACKGROUND OF THE INVENTION

Chlorinated aromatic compounds are of great importance industrially. They are used as intermediates, in particular for the manufacture of agrochemicals, dyes and non-flammable dielectric liquids.

Numerous methods exist allowing the introduction of one or more chlorine atoms into an aromatic nucleus but most industrial processes use chlorination by chlorine, which chlorination is catalysed by metal chlorides. The catalysts which can be used for this reaction are $AlCl_3$, $TiCl_4$, $SnCl_4$, $SbCl_3$, $SbCl_5$, $ZrCl_4$, $FeCl_3$, $NbCl_5$, $MoCl_5$, $WCl_6$, $GaCl_3$ or $TeCl_4$. The most generally used are $FeCl_3$, $AlCl_3$, $SbCl_3$ and $SbCl_5$.

The chlorination reaction is generally carried out by introducing gaseous chlorine into a reactor containing the aromatic hydrocarbon to be chlorinated and the catalyst or catalytic system. The chlorination temperature is generally between 40° C. and 120° C.

The reaction is generally carried out at atmospheric pressure. On completion of the chlorination reaction, the reaction mixture, hereinafter denoted as reaction crude, is subjected to degassing under an inert gas which allows the HCl content to be brought from several thousands of ppm to several hundreds of ppm.

The degassed reaction crude is subsequently washed with water, optionally basified water, which makes it possible to remove the catalyst. However, this operation exhibits many disadvantages, because it is necessary in particular to dry the washed reaction crude. In addition, this washing operation generates effluents containing in particular metal chlorides and organochlorinated or chlorinated aromatic compounds, the latter being carried away during the said washing because of their solubility in water. Thus, for example, the solubility in water of monochlorobenzene is 150 ppm, that of dichlorobenzenes is 70 ppm and that of trichlorobenzenes is 20 ppm.

These organochlorinated compounds can also be carried away mechanically, in the form of vesicles.

Due to current regulations regarding the discharge of industrial effluents, it is essential to treat these aqueous discharges in order to lower their content of organochlorinated compounds as well as of metal chlorides.

These treatment operations are expensive and few effective solutions have been provided.

Thus, in U.S. Pat. No. 4,885,418, provision is made to pass a reaction mixture originating from the chlorination of aromatic hydrocarbons in the presence of metal chlorides over a wet anionic resin in the hydroxyl form.

Although this process exhibits the advantage of being able to remove most of the metal chlorides, it however exhibits many disadvantages. This is because it is necessary to very thoroughly degas the reaction mixture in order to remove hydrochloric acid before passing over the anionic resin. Subsequently, the regeneration of the resins is expensive and requires use of aqueous hydrochloric acid solution and then aqueous sodium hydroxide solution and inevitably results in aqueous effluents which have to be treated. In addition, this process is entirely silent on the removal of organochlorinated compounds.

SUMMARY OF THE INVENTION

A process for the purification by distillation of chlorinated aromatic hydrocarbons obtained by chlorination of non-chlorinated or partially chlorinated aromatic hydrocarbons in the presence of ferric chloride $FeCl_3$ has now been found; the said process being characterized in that, before the distillation of the said chlorinated aromatic hydrocarbons, the reaction mixture or reaction crude is optionally partially degassed and that this optionally degassed reaction crude is distilled, preferably directly, in the presence of the $FeCl_3$.

Mention will be made, as illustration of non-chlorinated or partially chlorinated aromatic hydrocarbons denoted herein below by aromatic hydrocarbons, of toluene, mono- and dichlorotoluenes, para-xylenes, chloroxylenes, ortho-dichlorobenzene or trichlorobenzenes.

The chlorination process is known and can be carried out generally by introduction of gaseous chlorine into the aromatic hydrocarbon to be chlorinated containing $FeCl_3$. The chlorination operation is generally carried out at atmospheric pressure at a temperature of between 40° C. and 120° C. and preferably between 60° C. and 120° C.

According to the present invention, the reaction crude originating from the chlorination reaction of aromatic hydrocarbons in the presence of $FeCl_3$ is optionally partially degassed under a stream of inert gas, such as nitrogen, for example, at a temperature which is advantageously that of the chlorination or at a lower temperature and preferably atmospheric pressure.

According to the present invention, the chlorinated aromatic hydrocarbons are distilled in the presence of the $FeCl_3$ used in the chlorination reaction in an amount which can range from 10 to 300 ppm and preferably between 50 ppm and 200 ppm. It would not be departing from the scope of the invention if the $FeCl_3$ were combined with a cocatalyst containing sulphur, such as N-substituted phenothiazine derivatives (N-chloracarbonylphenothiazine).

According to the present invention, the optionally degassed reaction crude can be distilled (which distillation is carried out without the removal of $FeCl_3$ or the catalytic system containing same from the said optionally degassed reaction crude) either batchwise or continuously.

In the case where batchwise distillation is carried out, the optionally degassed reaction crude containing $FeCl_3$ is charged, preferably directly to a boiler of a distillation column. A mixture of unconverted aromatic hydrocarbons and residual hydrochloric acid and then subsequently the chlorinated aromatic hydrocarbons distill at the column top. The residue is composed of iron chlorides and heavy organochlorinated compounds.

When the distillation is carried out continuously, a distillation unit composed of several columns is fed with the optionally degassed reaction crude containing $FeCl_3$.

Partial degassing of the HCl is advantageous. For example, it minimizes the corrosion of a column made of mild steel. Accordingly, the more HCl that is degassed, the better, from the standpoint of corrosion. Therefore, the extent of degassing is variable, depending on the materials of construction.

According to a preferred form, a distillation unit composed of two columns is used.

A first column filled with a packing is fed with the degassed reaction crude containing a mixture composed of chlorinated aromatic hydrocarbons, unconverted starting aromatic hydrocarbons, $FeCl_3$ and traces of HCl.

A mixture composed of unconverted starting reactants and hydrochloric acid distils at the top of this first column. This mixture can be recycled to the chlorination reactor.

A mixture comprising the chlorinated aromatic products and iron chlorides is obtained at the column bottom.

A second column, which can exhibit the same characteristics as the first column, is fed with this mixture.

However, the distillation is preferably carried out with different temperature and pressure conditions, which depend on the physicochemical characteristics of the chlorinated products obtained.

The chlorinated products, optionally in the form of a mixture of isomers or as is, are distilled at the column tops and undesired overchlorinated products and iron chlorides are obtained at the bottom of the column; these bottoms, which can be extracted continuously or under batchwise conditions, are subsequently disposed of, in particular by incineration.

This process applies very particularly to the preparation of the chlorotoluenes and trichlorobenzenes obtained by chlorination respectively of toluene and dichlorobenzenes in the presence of $FeCl_3$.

Colourless products are obtained with a very low content of HCl and of $FeCl_3$.

In addition, no corrosion of the distillation equipment, which is made of simple materials, such as steel, and only a very slight fouling of the columns are observed after several months, indeed several years, of operation, which makes it possible to retain the efficiency of the separation of products having relatively close boiling points.

This fouling can advantageously be removed by a simple treatment with water of the column under consideration.

In addition, it is found that the distillation of the degassed reaction crude in the presence of the chlorination catalyst does not modify, by the operation of an isomerization reaction, the isomeric composition subjected to the said distillation.

The examples which follow illustrate the invention.

EXAMPLE 1

Dichlorotoluenes Obtained by Continuous Chlorination of Toluene in the Presence of $FeCl_3$ The reaction crude originating from the operation of a chlorination of toluene in the presence of $FeCl_3$ is subjected to partial degassing with nitrogen at a temperature of between 80° C. and 90° C. at atmospheric pressure.

This partially degassed reaction crude has the following composition (the percentages are expressed by weight):
ortho- and para-chlorotoluene: 80.7%,
2,3-, 2,4-, 2,5-, 2,6-, 3,4-dichlorotoluenes: 18.6%,
trichlorotoluenes: 0.7%,
HCl: 400 ppm and $FeCl_3$: 400 ppm.

A distillation column heated by means of 6-bar steam and filled with a Sulzer packing corresponding to an efficiency of 15 actual plates is fed continuously with this reaction crude. Feed is introduced at the middle of the column with a throughput of 2350 kg/h. The reflux ratio is 0.7.

Distillation is carried out under a pressure of 8000 Pa (60 mm of Hg). The bottom temperature is 122° C. and the top temperature is 76° C.

A liquid containing the ortho- and para-chlorotoluenes and traces of HCl is distilled at the top. This mixture is recycled to the chlorination reactor.

The liquid at the column bottom is composed of:
the mixture of dichlorotoluenes mentioned above,
the trichlorotoluenes,
the iron chlorides ($FeCl_3$ and $FeCl_2$)

An 18 m³ boiler of a distillation column composed of 30 bubble trays (15 actual plates) operating with 14-bar steam and under a pressure of 3,333 Pa (25 mm of mercury) is fed continuously with this mixture. The reflux ratio is 1.

The top temperature is approximately 100° C.

The boiler bottom temperature is 160 to 180° C.

A colourless liquid is obtained at the column top which has the following composition:
monochlorotoluene: 0.4%
2,5-dichlorotoluene: 26.4%
2,6-dichlorotoluene: 21.3%
2,4-dichlorotoluene: 36%
2,4-dichlorotoluene: 5.8%
2,3-dichlorotoluene: 10%
trichlorotoluenes: 0.1%
HCl content: 2.1 ppm
Hydrolysable chlorine content: 1.7 ppm (aliphatic chlorine).

This liquid product is entirely suitable for use as solvent or as dielectric liquid.

The product obtained at the column bottom, composed essentially of trichlorotoluenes and iron chlorides, gradually accumulates in the boiler and is extracted therefrom semi-continuously without this presenting any problem of extraction or even of fouling of the said boiler.

The extract is destroyed by incineration in an authorized centre for the destruction of chlorinated waste.

After operating for many years, no problem of corrosion of the materials constituting the distillation unit, which is made of ordinary steel, is observed.

Only a slight decrease in efficiency of the first column after approximately 3 to 4 months is observed. This efficiency is rapidly recovered if simple washing with refluxing water is carried out for a time equal to approximately 24 hours.

EXAMPLE 2

Purification of Trichlorobenzenes Obtained by Chlorination of Ortho-Dichlorobenzene in the Presence of $FeCl_3$ The reaction crude originating from the chlorination operation on ortho-dichlorobenzene in the presence of $FeCl_3$ is subjected to slight degassing with nitrogen. This degassing is carried out in a single tank, with a nitrogen throughput equal to 25 m³/h, at a temperature of between 75° C. and 80° C., at atmospheric pressure. This degassed reaction crude has the following composition (the percentages are expressed by weight):
ortho-dichlorobenzene: 75%
1,2,3- and 1,2,4-trichlorobenzenes: 24%
tetrachlorobenzenes: 1%
HCl: 200 ppm
$FeCl_3$: 200 ppm.

A distillation column heated by means of steam at 190° C. and filled with a structured packing of the Sulzer type (point-welded goffered plates) corresponding to an efficiency of 25 actual plates is fed continuously with this degassed reaction crude.

Feed is introduced at the middle of the column with a throughput of 2400 kg/h. The reflux ratio is 1.

Distillation is carried out under a pressure of 18,666 Pa (140 mm of Hg).

The column bottom temperature is 170° C. and the column top temperature is 120° C.

A liquid composed of ortho-dichlorobenzene (unconverted) containing a small amount of HCl distils at the top. This liquid is recycled to the chlorination reactor.

The liquid at the column bottom is composed of:

a mixture of isomers of trichlorobenzenes, tetrachlorobenzenes, pentachlorobenzene, iron chlorides ($FeCl_3$, $FeCl_2$)

A second distillation column having the same packing and the same characteristics as the first column (efficiency equal to 25 theoretical plates) is fed continuously with this mixture.

This column is fed at the middle of the column, the heating of which is provided by steam at 190° C. Distillation is carried out under a pressure of 6,666 Pa (50 mm of Hg). The temperature at the column top is 120° C. and at the column bottom 160° C.

A colourless liquid is obtained at the column top, with a throughput of 600 kg/h, which has the following composition:

ortho-dichlorobenzene: 0.15%

1,2,3- and 1,2,4-trichlorobenzenes: 99.84% tetrachlorobenzenes: 0.007%

HCl<10 ppm

This mixture of trichlorobenzenes can be used as solvent or non-flammable dielectric liquid or as basic starting material for the production of pure 1,2,3-trichlorobenzene and pure 1,2,4-trichlorobenzene.

The residue obtained at the column bottom is composed of a mixture of tetrachlorobenzenes, pentachlorobenzene and iron chlorides. This residue is continuously extracted (2.5 kg/h) and is subsequently, as in Example 1, incinerated in an authorized centre for the destruction of chlorinated waste.

Here again, after operating for many months, no corrosion of the materials constituting the 2 distillation columns is observed.

EXAMPLE 3

A comparative test is carried out which consists in comparing the efficiency of our process when the latter is applied to a mixture of trichlorobenzenes containing $FeCl_3$ (in accordance with the invention) or alternatively $AlCl_3$ or $SbCl_3$ (not in accordance with the invention).

The distillation is carried out of 800 g of a mixture composed of (the percentages are expressed by weight):

ortho-dichlorobenzene: 1.25%

1,2,4-trichlorobenzene: 82.35%

1,2,3-trichlorobenzene: 14.30%

1,2,4,6-tetrachlorobenzene: 0.5%

1,2,3,4-tetrachlorobenzene: 0.6% catalyst ($FeCl_3$, $AlCl_3$ or $SbCl_3$): 1%

This mixture is introduced into a glass round-bottomed flask surmounted by a 1.5 meter adiabatic column filled with a packing based on glass coils (7 actual plates).

Distillation is carried out continuously under a pressure of 6,666 Pa (50 mm of Hg) with a reflux ratio of 1. Heating is provided by a heating mantle and distillation is regulated by introducing nitrogen using a capillary tube.

Three fractions F1, F2 and F3 of 200 g are produced and 200 g are left in the bottom.

The top temperature is 120–123° C., whereas the bottom temperature is 130° C. The analysis of the fractions is reported in Table 1 below.

The following are reported in this table:

the colour of the fractions, the content of metal corresponding to the catalyst, the content by weight of $Cl^-$ (either in the HCl form or in the chlorides form).

The results for $AlCl_3$ have not been reported because distillation is impossible; there are numerous blockages at the column top.

TABLE 1

|  | $FeCl_3$ | | | $SbCl_3$ | | |
| --- | --- | --- | --- | --- | --- | --- |
| Color | F1 colorless | F2 colorless | F3 colorless | F1 colorless | F2 colorless | F3 colorless |
| Content of Fe | 0.4 ppm | 0.5 ppm | 0.6 ppm | — | — | — |
| Content of Sb | — | — | — | 1.81% | 0.26% | 0.047% |
| Content by weight of $Cl^-$ (%) | 0.0004 | <0.0001 | <0.0001 | 1.53 | 0.247 | 0.04 |

It is found that, although $FeCl_3$ and $SbCl_3$ have higher boiling points than the chlorinated aromatic hydrocarbons, only $FeCl_3$ remains in the column bottom.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In a process for the purification of a reaction crude of chlorinated aromatic hydrocarbons obtained by chlorination of non-chlorinated or partially chlorinated aromatic hydrocarbons in the presence of $FeCl_3$; the improvement comprising, partially degassing the reaction crude and distilling the resultant partially degassed reaction crude in the presence of the $FeCl_3$.

2. A process according to claim 1, wherein the non-chlorinated aromatic hydrocarbon is toluene.

3. A process according to claim 1, wherein the partially chlorinated aromatic hydrocarbon is ortho-dichlorobenzene.

4. A process according to claim 1, wherein the chlorinated aromatic hydrocarbons is a mixture comprising dichlorotoluenes and $FeCl_3$ originating from the chlorination of toluene in the presence of $FeCl_3$.

5. A process according to claim 1, wherein the chlorinated aromatic hydrocarbons is a mixture comprising trichlorobenzenes and $FeCl_3$ originating from the chlorination of ortho-dichlorobenzene in the presence of $FeCl_3$.

6. A process according to claim 1, wherein the resultant partially degassed reaction crude is directly subjected to distillation in the presence of $FeCl_3$.

7. A process according to claim 6, wherein the non-chlorinated aromatic hydrocarbon is toluene.

8. A process according to claim 6, wherein the partially chlorinated aromatic hydrocarbon is ortho-dichlorobenzene.

9. A process according to claim 6, wherein the chlorinated aromatic hydrocarbons is a mixture comprising dichlorotoluenes and $FeCl_3$ originating from the chlorination of toluene in the presence of $FeCl_3$.

10. A process according to claim 6, wherein the chlorinated aromatic hydrocarbons is a mixture comprising trichlorobenzenes and $FeCl_3$ originating from the chlorination of ortho-dichlorobenzene in the presence of $FeCl_3$.

11. A process according to claim 1, wherein the $FeCl_3$ during the distilling step is present in an amount of from 10 to 300 ppm by weight based on the amount of reaction crude introduced to the distilling step.

12. A process according to claim 11, wherein the amount of $FeCl_3$ is between 50 and 200 ppm by weight.

13. A process according to claim 1, wherein the distilling is conducted in a distillation unit composed of two columns in series and a bottom fraction from the first column is passed into the second column.

14. A process according to claim 13, wherein a mixture of partially degassed crude reaction product containing $FeCl_3$ is introduced into the middle of the first distillation column.

15. A process according to claim 14, wherein said bottom fraction from the first column contains $FeCl_3$ and said bottom fraction is passed into the middle of the second distillation column.

16. A process according to claim 1, wherein a mixture of partially degassed crude reaction product containing $FeCl_3$ is introduced into the middle of a distillation column.

* * * * *